(12) United States Patent
Li et al.

(10) Patent No.: US 11,896,358 B2
(45) Date of Patent: Feb. 13, 2024

(54) DEVICE AND METHOD FOR DYNAMIC SKIN IMPEDANCE MEASUREMENT AND CORRECTION

(71) Applicant: Wellness Allied Inc, Natick, MA (US)

(72) Inventors: Weihui Li, Natick, MA (US); Tao Zhang, Natick, MA (US)

(73) Assignee: Wellness Allied Inc, Dover, MA (US)

( * ) Notice: Subject to any disclaimer, the term of this patent is extended or adjusted under 35 U.S.C. 154(b) by 578 days.

(21) Appl. No.: 16/871,106

(22) Filed: May 11, 2020

(65) Prior Publication Data
US 2021/0345901 A1    Nov. 11, 2021

(51) Int. Cl.
*A61B 5/0531* (2021.01)
*A61B 5/00* (2006.01)

(52) U.S. Cl.
CPC .......... *A61B 5/0531* (2013.01); *A61B 5/7221* (2013.01); *A61B 5/742* (2013.01); *A61B 2562/0215* (2017.08)

(58) Field of Classification Search
CPC ............................ A61B 5/0531; A61B 5/7221
USPC ....................................................... 600/547
See application file for complete search history.

(56) References Cited

U.S. PATENT DOCUMENTS

| | | | |
|---|---|---|---|
| 2,829,638 A | 4/1958 | Douglas | |
| 4,895,163 A | 1/1990 | Libke et al. | |
| 5,879,308 A * | 3/1999 | Rasanen | A61B 5/0535 600/536 |
| 7,474,917 B2 * | 1/2009 | Jang | A61B 5/415 600/393 |
| 7,603,171 B2 | 10/2009 | Eror et al. | |
| 2004/0122336 A1 * | 6/2004 | Jang | A61B 5/415 600/547 |
| 2014/0350432 A1 * | 11/2014 | Khalfallah | A61B 5/4076 600/547 |
| 2015/0018707 A1 | 1/2015 | Bhatkar et al. | |

FOREIGN PATENT DOCUMENTS

CN         101489476 B       5/2011

* cited by examiner

Primary Examiner — Nicole F Lavert

(57) ABSTRACT

A skin impedance measuring device and method includes: an electrode system having at least two electrodes placed on the skin; an adjustable voltage output unit to generate forward and reverse voltages on the electrodes; a skin impedance measurement unit to measure electrical signals from the electrodes; a central processing unit and a computing memory for calculating forward and reverse skin impedances, determining whether the measurement results are abnormal, and correcting abnormal results by delivering additional DC or AC voltages of adjustable magnitudes and frequencies based on impedances; and a display unit.

17 Claims, 7 Drawing Sheets

(b)

DEVICE AND METHOD FOR DYNAMIC SKIN IMPEDANCE MEASUREMENT AND CORRECTION

TECHNICAL FIELD

The present invention is related to the skin impedance measurement technology in the medical field.

BACKGROUND

Up to today, many scientific or clinical workers have conducted a large number of studies to measure skin impedance and proposed some methods and theories on using skin impedance as a way to assess human health conditions.

In 1849, German Dubois-Reymond discovered for the first time that human skin demonstrated electrical activity. In 1878, Hermann and Luchsinger in Switzerland discovered that sweating was an important factor affecting skin impedance. In 1879, Vigouroux in France discovered that there are correlations between skin impedances and psychological activities. The above studies can be found in Literature 1. U.S. Pat. No. 2,829,638A proposed a method to monitor people's arousal and the emotion change through measuring skin impedance.

In addition to the application of skin impedance in the field of psychology, U.S. Pat. No. 4,895,163A uses a two-electrode measuring system to estimate the body fat percentage. U.S. Pat. No. 7,603,171B diagnoses lung cancer based on skin impedance from selected body areas. Patent application US20150018707A1 makes use of skin impedance to determine body pain severity.

The inventors of the present invention studied the existing technologies and concluded that the skin impedance changes with the frequency of exciting power, the time duration of the measurement, and the properties of measuring electrodes.

First, the skin impedance changes with the exciting power frequency. According to Literature 2, the typical skin impedance is 500K $\Omega/cm^2$. The research in Literature 3 shows that the skin impedance ranges from 10K to 1 M $\Omega/cm^2$ at 1 Hz power. When the frequency is increased to 1 MHz, the skin impedance drops to about 300 $\Omega/cm^2$. In addition, the research in Literature 4 shows that the skin impedance gradually decreases with increasing measurement time duration.

With more research conducted, people also observed the electrode polarization phenomenon during skin impedance measurement. This is related to the half-cell potential fluctuations. FIG. 1 is the equivalent circuit for the electrode skin interface (Literature 5). $R_d$ and $C_d$ represent the resistance and capacitance of the electrode-skin interface. $R_s$ is the resistance associated with the electrode. $E_{hc}$ is the half-cell potential. According to Literature 6, the electrode used in the measurement of skin impedance is equivalent to a transducer between the electron flow in the wire and the ions flow inside the body. In theory, there are two types of electrodes: a polarizable electrode ideally having no current flows through the metal-electrolyte interface, analogous to an ideal capacitor; a non-polarizable electrode ideally having no polarization but having free current flow, analogous to a resistor. In reality, all the electrodes are between a completely polarizable electrode and a completely non-polarizable electrode. Taking the Ag/AgCl electrode as an example, it consists of two layers: one layer is the metal silver, the other layer is metal ionic component AgCl coated on the top of Ag. In addition, electrolyte gel is often applied between the electrode and the skin for better contact. According to Literature 7, when the electrode is in contact with the electrolyte, metal cations will be reduced to the metal on the negative electrode, and excessive chloride anions will accumulate around to form an electrical double-layer. On the positive electrode, metal will be oxidized to form metal cations into the electrolyte layer, forming an electrical double-layer as well. When the external potential is applied to the skin to form current, the voltage on the double-layers is called half-cell potential, or the electrode polarization. When the electrodes are completely non-polarizable, the electrode has a stable half-cell potential, and the electrode is an analogy to the resistor. According to Literature 7, the silver/silver chloride electrode is one of the electrodes closest to the non-polarizable electrode.

According to Literature 8, the equivalent circuit of the skin is shown in FIG. 2. The skin consists of three layers of tissue: epidermis, dermis, and subcutaneous layers. Part of epidermis resembles a semi-permeable ionic half membrane that generates a skin potential: Ese. The remaining part of the epidermis is equivalent to a parallel RC circuit, which is series with Ese. The dermis and subcutaneous layers have good electrical conductivity. They can usually be considered as pure resistors, which is represented by $R_u$ here. In addition, a corresponding potential $E_p$, and a RC network of $R_p$ and $C_p$ are generated between the sweat glands and the subcutaneous tissue. The $E_p$, $R_p$, and $C_p$ of the sweat glands can usually be ignored.

According to the research in Literature 9, the skin impedance mainly depends on the tissue structure and the frequency of the current applied to the skin. When the frequency is less than 1 KHz, the skin high impedance mainly depends on the impedance of the stratum corneum. At higher frequency, like 1 MHz, the skin impedances decrease, even though the stratum corneum still dorminates.

Existing methods for measuring skin impedance usually use a constant voltage source or a constant current source. FIG. 3 shows the principle of conventional skin impedance measurement using a constant voltage source. Specifically, during skin impedance measurement, a resistor $R_1$ is connected in series with the skin impedance. A DC or AC voltage is then applied. Using the voltage divider principle, the voltage across the resistor $R_1$ and the voltage between these two electrodes on the skin are measured; the skin impedance $R_s$ is then calculated. FIG. 4 shows the principle of conventional skin impedance measurement using a constant current source. Specifically, during the skin impedance measurement process, a DC or AC constant current source is applied between the skin electrodes, and the voltage between the skin electrodes is measured to obtain the characteristics of the relevant skin impedance $R_s$.

FIG. 5 shows another implementation of skin impedance measurement with a constant voltage source Vcc applied to the stimulating electrode (Literature 10). The stimulating electrode and the reference electrode are attached to the skin to measure the skin impedance Rs. The stimulating electrode has a voltage of Vcc. Vcc drops on Rs, R1 and Op-Amp A and has an output of V0. V0 is then fed back to the input terminal Vb of Op-Amp A through R3, R2 and Op-Amp B. The reference potential on the non-inverting input terminal of Op-Amp B is obtained from a voltage divider circuit R5 and R4. C4 is used to eliminate the noise of the Op-Amp B reference potential. C3 is used to eliminate the noise on the stimulating electrode. C1 and C2 are used with R1 and R2 respectively to form the low-pass filters. This design has an advantage: when R2=R3, R4=R5, the skin impedance can be calculated by measuring V0 and Vb voltage, with the formula Rs=R1*(Vcc−Vb)/(Vb−V0). In addition, the design of the circuit ensures that the range of V0 is between 0 and Vcc/2, and the range of Vb is between Vcc/2 and Vcc. This guarantees that the difference between Vb and V0 is between 0 and Vcc, and in theory, any skin impedance value between 0 and infinity can be measured.

SUMMARY

The conventional method to measure skin impedance with DC constant voltage source or DC constant current source cannot guarantee the reliability and reproducibility (or consistency) of the results. This is mainly caused by the following factors: (1) the above mentioned electrode polarization phenomenon and half-cell potential; (2) the existence of biopotential in biological tissues, such as the internal potentials Ep and Ese of the skin; (3) lack of measurement standards, such as measuring time duration and measuring electrodes; (4) lack of consideration for the heterogeneous structure of the biological tissue, primary or secondary to the external stimulating current, which will cause the distortion of the measurement results.

Besides DC sources, there are technologies that use an AC constant voltage source or an AC constant current source for skin impedance measurement to reduce the effects of polarization. However, the use of an AC constant voltage source or an AC constant current source has two problems: 1) if the AC frequency is relatively low, it needs at least a few cycles to perform the measurement, hence requiring longer measurement duration. It is not ideal to capture transient changes of skin impedance; 2) if the AC frequency is relatively high, the impedance measured between these two skin electrodes comes more from the underneath body tissue, and less from the skin. It will not be significant to detect the capacitance part of the impedance from the skin and thus not significant to compare them between different body parts. Therefore, in practical applications, it is still more common to use an DC constant voltage source or an DC constant current source.

Patent CN101489476B and CN106413544A proposed a method of measuring resistance Rp, capacitance Cp, and resistance Rs in an equivalent circuit using a biphasic pulse current source. The calculations in these two patented technologies are both based on bi-directional constant DC current source to obtain skin impedance. It has at least two disadvantages: 1) when the skin impedance is very large, to maintain the constant current, the voltage applied to the skin could be too large for the human body; 2) if the intrinsic voltage of the power source is reached, the stimulating voltage will be saturated and the constant stimulating current will be no longer constant. In addition, the measurement methods in these two patents only explain how to measure the skin impedance using a biphasic constant current source. They did not evaluate the polarization degree, nor did they take action to correct the polarization for better measurement results.

In view of the problems existing in measuring skin impedance by a DC constant voltage or current source, the present invention proposes a new measurement circuit and method to solve the above problems and improve the reliability of skin impedance measurement. The new circuit and method include: an adjustable DC voltage output unit, instead of a DC current output unit, is used so that the voltage saturation situation will not happen; the adjustable DC voltage output unit generates step-function DC voltages of different magnitudes that are within the safe range for human; step-function DC voltages of different magnitudes are applied to a stimulating electrode, forming a forward or reverse voltage between the stimulating electrode and reference electrode; the forward skin impedance and reverse skin impedance can be calculated with the forward and reverse DC voltages on the skin; the forward and reverse impedances are evaluated to determine whether the measurements are abnormal; if abnormal, correct the results by adjusting subsequent DC voltages with varied magnitudes and/or time durations through the stimulating electrode to the skin to eliminate or reduce the electrode/tissue polarization effects and ensure the accuracy of the measurement results; if the polarization effects cannot be reduced to a normal range, both values are recorded and their arithmetic and geometric averages are calculated to estimate the skin impedance; during the whole process, the current flowing through the skin is limited through a protective resistor to ensure the current applied to the skin does not exceed a safe upper limit.

According to an aspect of the present invention, a skin impedance measuring device is provided, which is comprised of: an adjustable voltage output unit to output step-function DC voltages, which is conducted to the skin through a stimulating electrode and a reference electrode, forming forward or reverse voltages between them; the adjustable voltage output unit can also be used to output AC voltages with adjustable amplitudes and frequencies, which are conducted to a local area of the skin through electrodes to form alternating voltages on the two measuring electrodes; an electrode system with at least two electrodes, which is placed on the skin to transmit the voltage from the adjustable voltage output unit to the measurement points; a skin impedance measurement unit for measuring electrical signals from the measurement point to obtain the skin impedance; a microcontroller processor; and a computing memory that stores instructions executed by the processor; when executed by the processor, the instructions include the steps of: calculating the difference between the forward skin impedance measured using forward DC voltages and the reverse skin impedance measured using reverse DC voltages; based on continuous measurement of forward skin impedance, reverse skin impedance and their differences, determining whether the measurement results are abnormal; for abnormal situations, correcting the results by adjusting the magnitudes and/or the time durations of the subsequent forward and reverse DC voltages, and/or applying additional AC voltages of adjustable magnitudes and frequencies to the electrode system; remeasuring the impedances to check if the measurement accuracy is improved; storing the skin impedances for future analysis; and a display unit for displaying the measurement results.

Optionally, when the instruction is executed by the processor, and when the difference between the forward and reverse impedances cannot be corrected to a preset range, the execution step further includes: calculating arithmetic and geometric averages of the forward skin impedance and the reverse skin impedance to estimate the skin impedance and store these data to serve as guidelines for future diagnosis and treatment.

Optionally, the electrode is a silver/silver chloride electrode.

Optionally, the electrode is a polarized electrode.

Optionally, the electrode is a metal electrode.

Optionally, the electrode measurement is a two-electrode measurement method.

Optionally, the electrode measurement is a multi-electrode measurement method.

Optionally, the electrode includes a stimulating electrode and a reference electrode, and the adjustable voltage output unit generates step-function DC voltages and applies to the stimulating electrode to form forward and reverse DC voltages between the stimulating electrode and the reference electrode.

Optionally, the adjustable voltage output unit includes one or more of the following components: a waveform generator, or a digital output from a microcontroller processer followed by digital-to-analog converters (DAC), and a current drive circuit, activated when the magnitude of the generated current from the DC voltage is below a predetermined threshold.

Optionally, the skin impedance test unit is configured to include an amplification and filter circuit and an A/D converter in the case of measuring one channel of skin impedance; in the case of measuring multiple channels of skin impedances, it is configured to have a voltage multiplexer, in addition to the amplification and filter circuit and the A/D converter.

Optionally, the variables to control the voltage output unit include: the time durations of the forward voltage and the reverse voltage applied between the electrodes.

Optionally, the variables to control the voltage output unit include: the magnitudes of the forward voltage and the reverse voltage applied between the electrodes.

Optionally, changing the time durations of the forward voltage and the reverse voltage applied between the electrodes includes one or more of the following measures: increasing the time duration of the forward voltage; decreasing the time duration of the forward voltage; increasing the time duration of the reverse voltage; decreasing the time duration of the reverse voltage.

Optionally, changing the magnitudes of the forward voltage and the reverse voltage applied between the electrodes includes one or more of the following measures: increasing the amplitude of the forward voltage; decreasing the amplitude of the forward voltage; increasing the amplitude of the reverse voltage; decreasing the amplitude of the reverse voltage.

Optionally, generating the controlling signal to control the adjustable voltage output unit includes: outputting step-function DC voltages of different amplitudes and time durations to form forward or reverse voltages; outputting AC voltages before or after the DC voltages to minimize polarization.

Optionally, the AC voltage is a square wave, a triangular wave, a sine wave, or other waveforms whose frequency and amplitude can be changed.

Optionally, the method further includes generating controlling signals to control the adjustable DC voltage output unit when the measurement results are abnormal, to output AC voltages of different frequencies and magnitudes, as a treatment method, to minimize skin impedance abnormalities.

According to another aspect of the present invention, a method for measuring skin impedance is provided, including (a) applying step-function DC voltages with adjustable magnitudes and time durations on a stimulating electrode, and forming forward and reverse voltages between the stimulating and reference electrodes, and conducting them through the electrodes to a local area of the skin; (b) measuring forward skin impedance and reverse skin impedance; (c) determining whether the measured data are abnormal based on the difference between the forward and reverse skin impedance; (d) if the measurement data are determined to be abnormal, correcting the results by adjusting the forward and reverse voltage magnitudes and time durations or delivering additional AC voltages of adjustable frequencies and time durations to improve the skin impedance measurement accuracy.

According to another aspect of the present invention, a method for measuring skin impedance is provided, further including: if it is still not possible to reduce the difference between forward and reverse skin impedance to a preset range, the forward skin impedance and reverse skin impedance values are averaged to estimate the skin impedance actual value.

The present invention solves (or at least partially solves) the previous problems of skin impedance measurement: (1) In the process of measuring the skin impedance with electrodes, the measurement results often deviate from the actual value due to electrode polarization and/or tissue polarization under a DC electric field. The present invention applies step-function DC voltages to the stimulating electrode, resulting in forward or reverse voltages on the two electrodes attached to the skin. If the difference between the measured values of forward skin impedance and reverse skin impedance keeps changing and is greater than a certain threshold, it is determined that the measured skin impedance is abnormal and there exists electrode and/or tissue polarization. This has never been done with traditional skin impedance measurement techniques. (2) When the skin impedance results are found to be abnormal, change the magnitudes and/or the time durations of the step-function DC voltages and/or apply additional AC voltage of adjustable frequencies and magnitudes to the stimulating electrode. This will alter the degree of the electrode and/or tissue polarization, resulting in more accurate skin impedance measured through the forward DC voltage and reverse DC voltage, thereby ensuring the accuracy of impedance measurement. (3) If the abnormal results cannot be corrected through the above method, the true skin impedance will be estimated by the arithmetic and geometric average of the forward skin impedance and the reverse skin impedance. (4) During the measurement/correction of skin impedance through DC or AC stimulation, the system also provides electrical stimulation treatment for the body or provide a therapeutic guideline for the following diagnosis and treatments.

DETAIL DESCRIPTION

The technical solutions of the present application will be further described below with reference to the accompanying drawings and specific embodiments. It can be understood that the specific embodiments described herein are only used to explain the present application, rather than limiting the present application.

Figure 6:
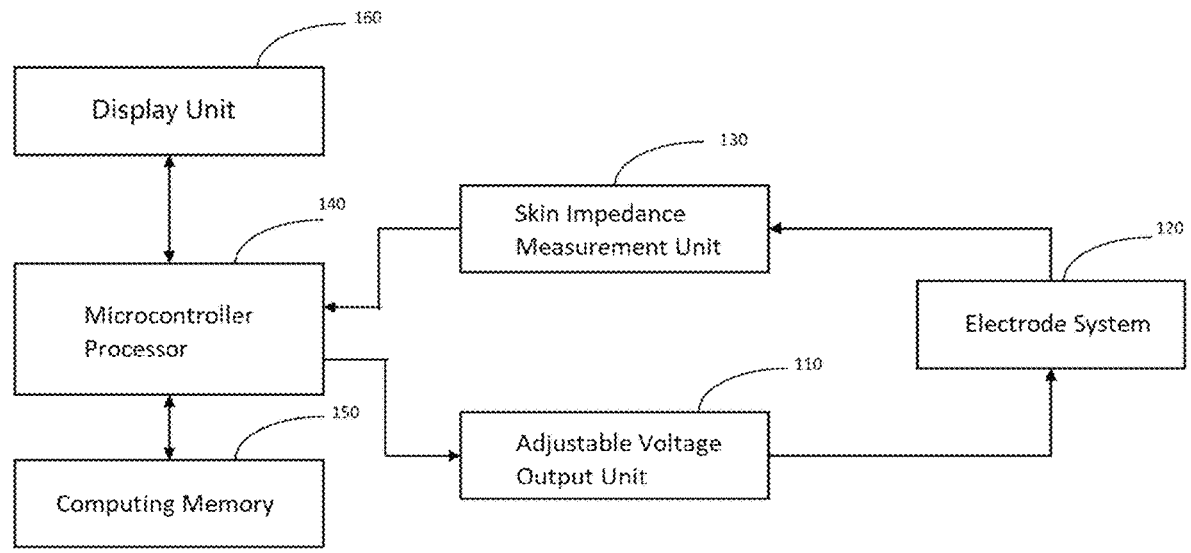
FIG. 6 is a structural diagram showing a skin impedance measurement device according to an embodiment of the present invention.

FIG. 6 is a block diagram showing a structural composition of a skin impedance measurement device according to an embodiment of the present invention.

As shown in FIG. 6, the skin impedance measurement device 100 includes: an adjustable voltage output unit 110, an electrode system 120, a skin impedance measurement unit 130, a processor 140, a memory 150, and a display unit 160.

It should be noted that these components can be integrated or distributed. For example, the memory can include cloud storage, which can store huge data, and then use artificial intelligence technology to perform big data analysis and discover patterns.

The adjustable voltage output unit 110 is used to output step-function DC voltages of different magnitudes or AC voltages of adjustable amplitudes and frequencies, which is transmitted through electrodes to form forward or reverse voltages or alternating AC voltages on a local skin area.

Figure 7A:
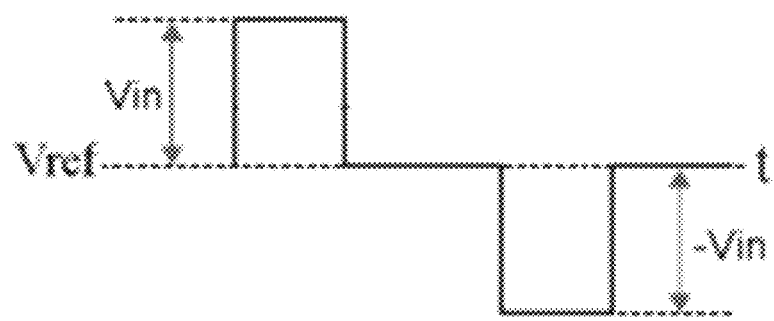
FIG. 7A shows examples of the waveforms for the forward DC voltage Vin and a reverse DC voltage—Vin across the skin when step-function DC voltages of different magnitudes applied to the stimulating electrode according to an embodiment of the present invention.

FIG. 7A shows a schematic waveform of a forward DC voltage Vin and a reverse DC voltage—Vin formed by applying step-function DC voltages of different magnitudes to the skin through electrodes according to an embodiment of the present invention. $V_{ref}$ is a reference voltage, and the reference voltage may be zero or a non-zero voltage. There can be a time interval between the forward DC voltage and the reverse DC voltage as shown in the figure, or there can be no time interval and directly jump from forward to reverse voltages.

As an example, the adjustable DC voltage output unit includes a waveform generator, or a digital output from a microcontroller processer followed by digital-to-analog converters (DAC); in addition, if the driving current is not large enough, the adjustable DC voltage output unit also includes a current drive circuit. If there are multiple channels of signals to be measured, the adjustable DC voltage output unit also includes multiplexer.

The electrode system 120 has at least two electrodes placed at measurement points on the skin to transmit voltages from an adjustable DC voltage output unit to the skin measurement points.

In one example, the electrodes are non-polarizable electrodes represented by silver/silver chloride electrode.

As an example, the electrodes used in the measurement process can be measured in a conventional two-electrode manner. In addition, the electrodes used in the measurement process can be measured using multi-point electrodes.

The skin impedance measurement unit 130 is configured to measure an electrical signal associated with two measurement points, thereby obtaining the skin impedance. Specifically, when the forward voltage is applied to the electrodes by the adjustable voltage output unit 110, the forward skin impedance is measured, and the reverse skin impedance is measured when the reverse voltage is applied to the electrodes by the adjustable voltage output unit 110.

In one example, if only one skin impedance is measured, the skin impedance measurement unit 130 may include an amplification and filter circuit and an A/D converter; if multiple skin impedances are to be measured, the skin impedance measurement unit 130 further includes a multiplexer.

Figure 7B:
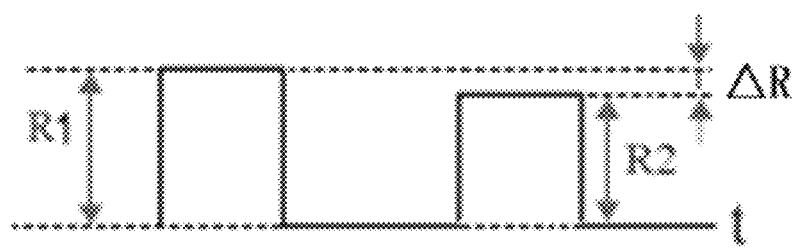
FIG. 7B schematically shows the corresponding measured forward skin impedance R1 and reverse skin impedance R2.

FIG. 7B schematically shows the measured forward skin impedance R1 and reverse skin impedance R2.

The processor 140 may be a general-purpose computer processor or microcontroller processor, or a customer designed integrated circuit.

Figure 8:
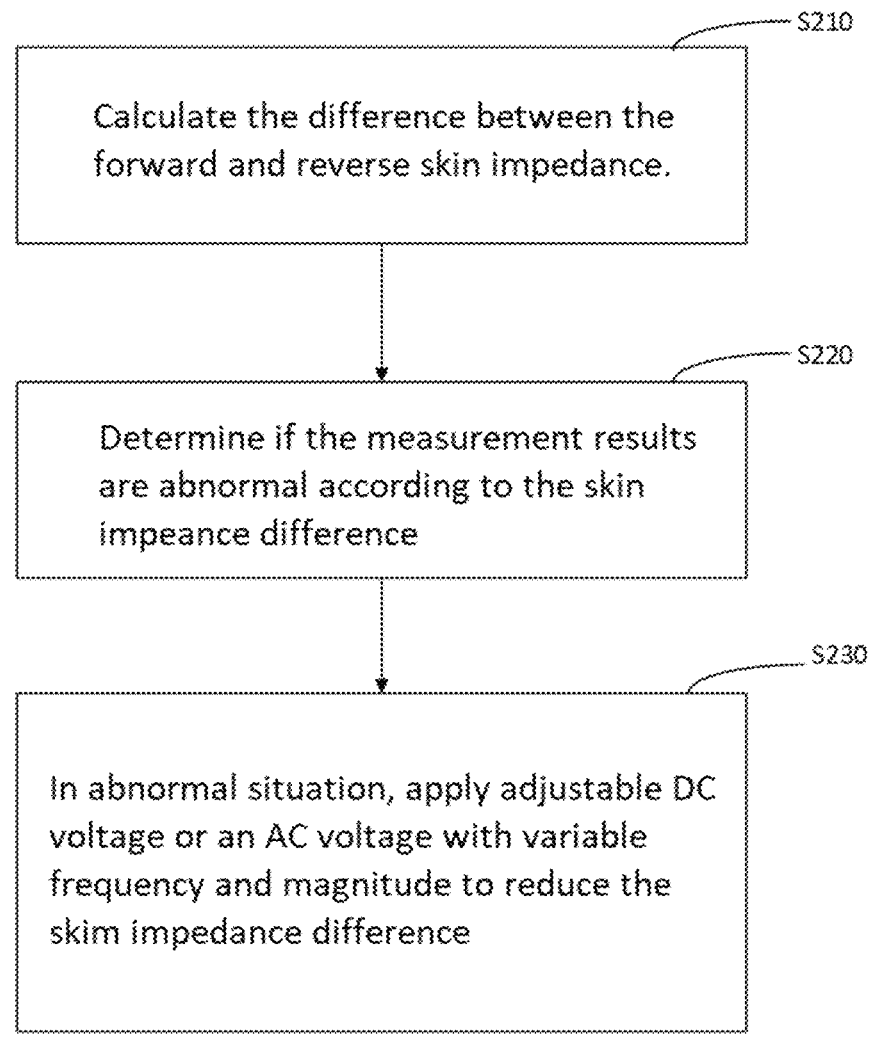
FIG. 8 shows a flowchart of a method for determining and correcting skin impedance abnormality executed by a computer executable program according to an embodiment of the present invention.

The memory 150 stores instructions executed by the processor, and when the instructions are executed by the processor, the method 200 illustrated in FIG. 8 is executed.

In step S210 of the flowchart shown in FIG. 8, the difference between the forward skin impedance measured using the forward DC voltage and the reverse skin impedance measured using the reverse DC voltage is calculated.

The difference $\Delta R$ between the forward skin impedance and the reverse skin impedance is schematically shown in FIG. 7B. The impedance difference $\Delta R$ can be positive or negative.

In step S220, it is determined whether the measurement result is abnormal based on the continuously measured forward skin impedance, reverse skin impedance, and their differences.

For example, with a threshold being preset, when the absolute value of the difference between the positive and negative impedances keeps changing and is beyond than a range, the system considers the measurement data being abnormal.

In step S230, for abnormal results, the system further calculates the amplitudes and/or time durations of the subsequent forward and reverse DC voltages, generates a controlling signal that controls the adjustable voltage output unit to output corresponding voltages to the electrodes, to ensure the accuracy of the measurement data.

In one example, the variables of the adjustable voltage output unit include the magnitudes of the forward voltage and the reverse voltage applied between the electrodes.

For example, changing the magnitudes of the forward voltage and the reverse voltage applied between the electrodes includes one or more of the following measures: increasing the magnitude of the forward voltage; decreasing the magnitude of the forward voltage; increasing the amplitude of the reverse voltage; decreasing the amplitude of the reverse voltage.

Figure 9A:
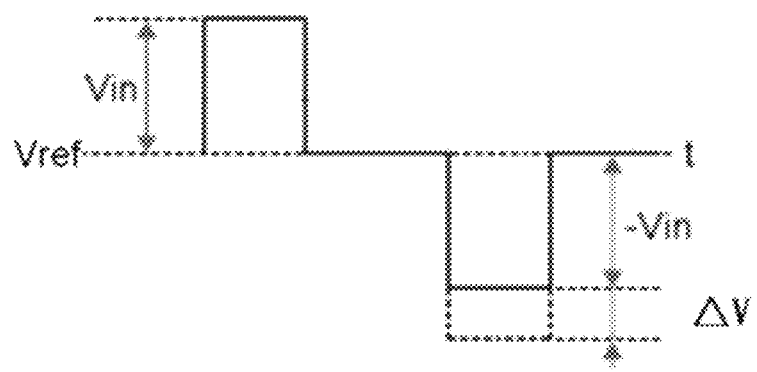
FIG. 9A schematically shows that the magnitude of the reverse voltage is increased by $\Delta V$.

FIG. 9A schematically shows that the magnitude of the reverse voltage is increased by $\Delta V$. Here, the value of $\Delta V$ can be calculated with algorithms based on past experience. Preferably, the differences between the forward skin impedance and the reverse skin impedance can be collected continuously and collectively among population. The big data can be analyzed through machine learning technology to discover the patterns.

In one example, the variables of the adjustable voltage output unit include the time duration of the forward voltage and the reverse voltages applied between the electrodes.

For example, changing the time durations of the forward voltage and the reverse voltage applied between the electrodes includes one or more of the following measures: increasing the time duration of the forward voltage; decreasing the time duration of the forward voltage; increasing the time duration of the reverse voltage; decreasing time duration of the reverse voltage.

Figure 9B:
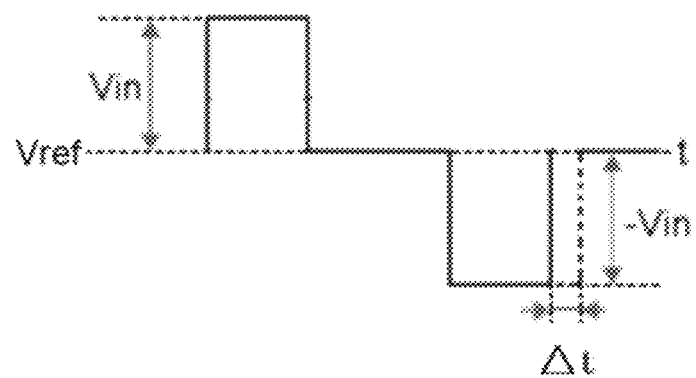
FIG. 9B schematically shows that the time duration of the reverse voltage is increased by $\Delta t$.

FIG. 9B schematically shows that the time duration of the reverse voltage is increased by Δt.

In one example, generating a controlling signal to control the adjustable voltage output unit includes: outputting forward and reverse DC voltages with different magnitudes and time durations.

In addition, before or after outputting step-function DC voltages with different amplitudes and time durations, AC voltages can be applied to reduce the degree of polarization of the system.

The AC voltage can be a square wave, triangle wave, sine wave, or other waveforms with adjustable frequencies and amplitudes.

In one example, when the measurement result is abnormal, the skin impedance measurement device generates a controlling signal that controls the adjustable voltage output unit, so that the adjustable voltage output unit outputs AC voltages with adjustable frequencies and amplitudes. The AC voltage stimulates the subject to minimize the polarization phenomena. At the same time, different combinations of AC voltages with adjustable frequencies and amplitudes can also be used for tentative treatment of the subject.

The display unit 160 is used for displaying measurement results, including the forward impedance, the reverse impedance, the difference between these two, signs indicating whether the measurement results are abnormal, signs indicating that the system is under skin impedance measurement or polarization correction, and the final measurement result for the skin impedance. The display unit 160 can also display words or signs to guide the user to operate.

Figure 10:
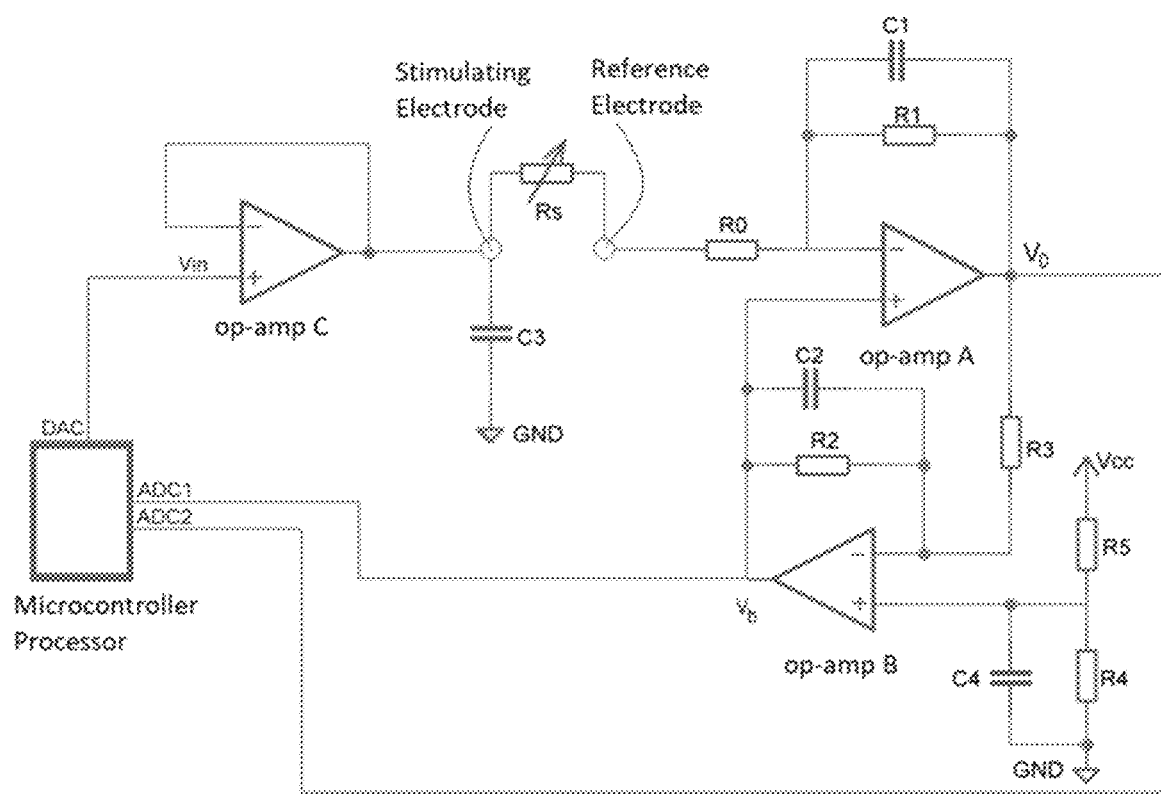
FIG. 10 schematically illustrates a circuit diagram for measuring skin impedance according to an embodiment of the present invention.

FIG. 10 is a schematic diagram showing a circuit diagram for measuring skin impedance according to an embodiment of the present invention. The electronic parts connection and working process will be described according to the drawings.

The stimulating electrode and the reference electrode are applied to two points on the skin to measure the skin impedance Rs. The voltage on the stimulating electrode is an adjustable DC voltage of value Vin. R0 is a protection resistor to prevent overload current generated when the stimulating electrode and reference electrode are short-circuited or when the skin impedance becomes too small. The stimulating electrode voltage Vin passes Rs, R0, and V0 through the op-amp A to generate an output V0. At the same time, V0 is fed back to the non-inverting input terminal Vb of op-amp A through op-amp B, R3 and R2. The reference potential of op-amp B is obtained by a voltage divider network formed by R5 and R4. C4 is used to eliminate the noise of the reference potential of the op-amp B. C3 is used to eliminate noise on the stimulating electrode. C1 and C2 form filters with R1 and R2 respectively, to form a low pass filter.

Figure 1:
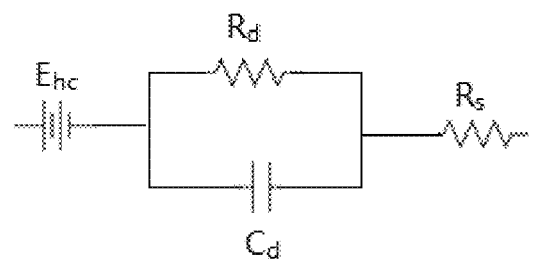
FIG. 1 shows an equivalent circuit of the electrode and skin interface.
Figure 2:
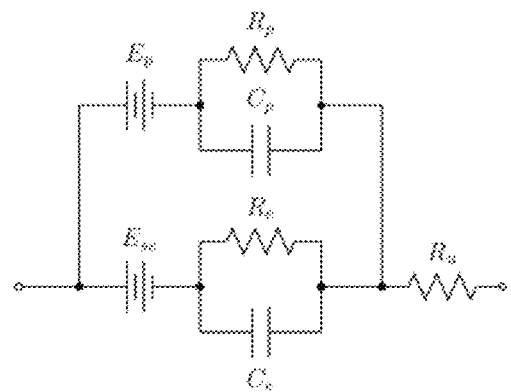
FIG. 2 shows an equivalent circuit of the skin.
Figure 3:
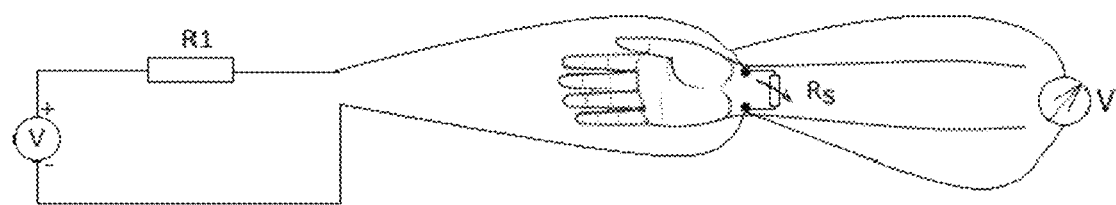
FIG. 3 shows a basic principle of measuring skin impedance using a constant voltage source.
Figure 4:
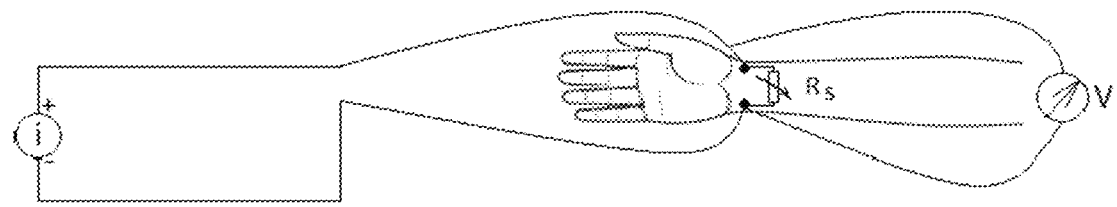
FIG. 4 shows a basic principle of measuring skin impedance using a constant current source.
Figure 5:
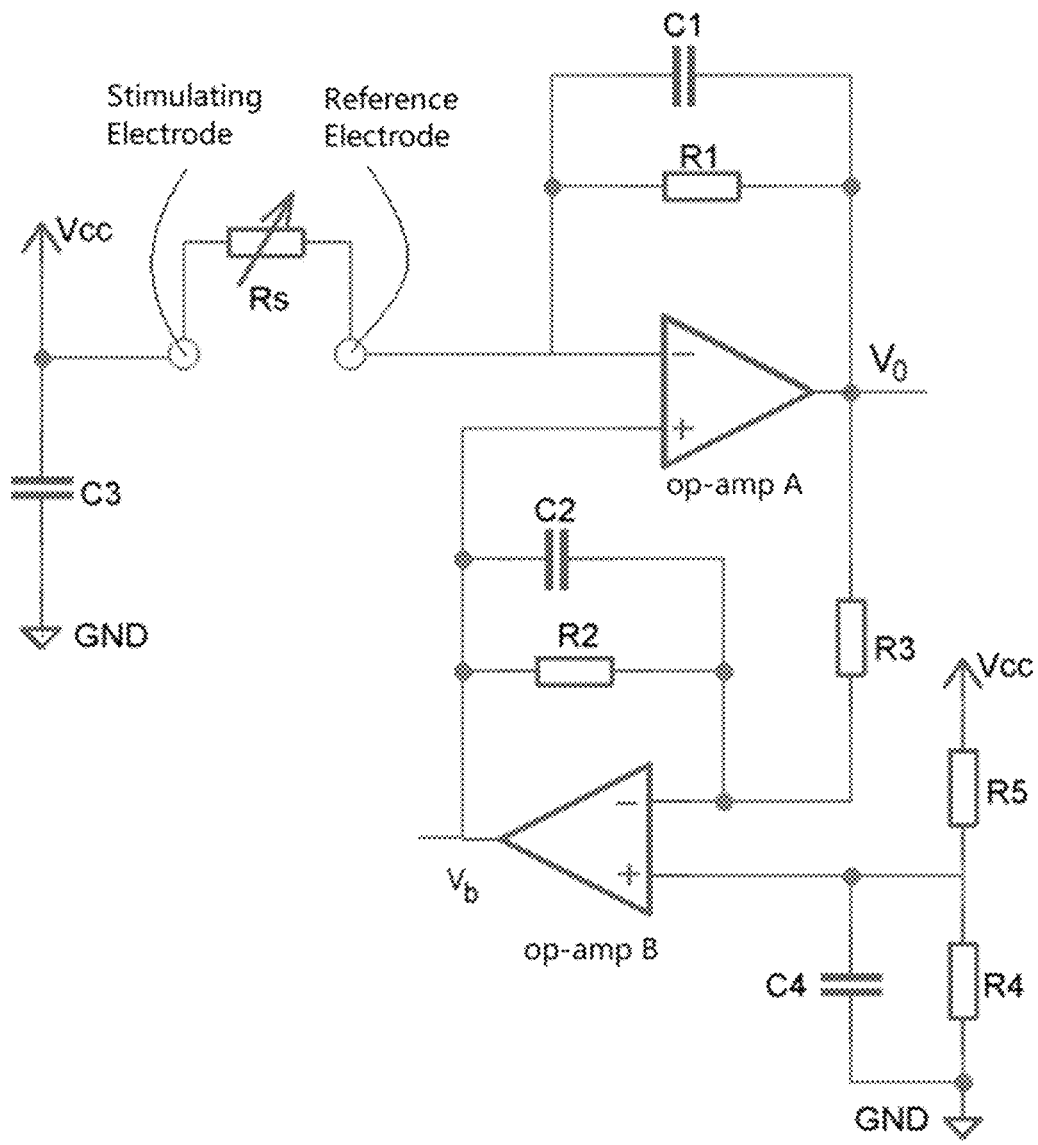
FIG. 5 shows another schematic diagram of measuring skin impedance with a constant voltage source. In the example, a system voltage Vcc is applied to a stimulating electrode.

Compared with FIG. 5, in addition to adding a protection resistor R0 to the original design, a more important improvement is that the voltage applied to the stimulating electrode is an adjustable voltage. The adjustable voltage can be generated through waveform generator or the microcontroller processor followed by D/A converter. If multiple channels of impedance are measured, a multiplexer is used to switch the voltage stimulation to different stimulating electrodes. If the output current is not big enough, op-amp C is needed for amplification, as the current drive circuit. In this circuit, the initial maximum DC voltage applied to the stimulating electrode is Vcc, the minimum initial reverse voltage is 0, and the reference voltage Vref is Vcc/2. The reference voltage Vref can also be set as 0. But this will require positive and negative power supplies in order to form forward and reverse voltages on the local skin areas. It will increase the cost.

According to another embodiment of the present invention, a method for accurately measuring skin impedance is provided, including the following steps: (a) apply step-function adjustable DC voltages on a stimulating electrode and form forward or reverse voltages between the stimulating and reference electrodes on the local skin area; (b) measure the forward skin impedance and reverse skin impedance under the forward and reverse potentials respectively; (c) determine whether the measured data is abnormal based on the difference between the forward and reverse skin impedance; (d) when determine that the measurement data results are abnormal, correcting the results by adjusting the step-function DC voltages or applying additional AC voltages of adjustable frequencies and magnitudes, and conducting the corresponding voltages to a local area of the skin through the electrodes to form a forward or reverse voltages or AC voltages, to minimize the polarization; (e) when the measurement data is abnormal and the difference between the forward skin impedance and the reverse skin impedance cannot be reduced to a preset range through a series of depolarization processes, the system records the value of forward skin impedance and reverse skin impedance, and the actual skin impedance can be estimated by weighted arithmetic and geometric averages.

The present invention solves (or at least partially solves) the previous problem of skin impedance measurement: (1) in the past, the skin impedance is often measured under constant DC electrical field. Due to the influence of electrode polarization and human cells polarization, the measurement results often deviate from the actual value. The skin impedance measurement method proposed by the present invention applies adjustable step-function DC voltages on the stimulating electrode to form forward or reverse voltages between the stimulating and reference electrodes and measures the corresponding forward skin impedance and reverse skin impedance. The difference between the forward skin impedance and reverse skin impedance is then calculated to determine if the skin impedance measurement results are abnormal. With this test method, it is easy to determine whether the electrode and/or skin has gone through polarization. This has never been done before with traditional skin impedance measurement techniques; (2) when the skin impedance result is abnormal, following methods are taken, trying to minimize the polarization: changing the time durations of the forward voltages and the reverse voltages applied; changing the step-function DC voltages which will change the magnitudes of the forward and reverse voltages applied; or applying AC voltages of adjustable frequencies and magnitudes. With these methods, the system electrodes can be restored to the initial equilibrium state. The body tissue can also be depolarized. Therefore, a relative more accurate measurement results can be achieved; (3) in addition, according to the skin impedance measurement technology of the present invention, when the skin impedance result is found to be abnormal, and it cannot be corrected by the above methods, the actual skin impedance will be estimated by averaging the forward skin impedance and the reverse skin impedance.

The embodiments of the present invention have been described above, the above description is exemplary, not exhaustive, and is not limited to the disclosed embodiments. Many modifications and variations will be apparent to those skilled in the art without departing from the scope and spirit of the embodiments described. Therefore, the protection scope of the present invention shall be subject to the protection scope of the claims.

The invention claimed is:

1. A skin impedance measuring device, comprising:
   an adjustable voltage output unit, configured to output step-function DC voltages with adjustable magnitudes, which are conducted to a local skin area through electrodes to form forward or reverse voltages; or configured to output AC voltages with adjustable magnitudes and frequencies, which are conducted to a local skin area through electrodes to form alternating voltages; and
   the adjustable voltage output unit comprises one or more of the following devices —waveform generator, digital signal generator with digital-to-analog converter (DAC); and, a current-drive circuit, activated when the magnitude of the driving current is below a predetermined threshold;
   an electrode system, having at least two electrodes placed at measurement points on the skin to conduct the voltages from the adjustable voltage output unit to related measurement points;
   a skin impedance measurement unit, configured to measure electrical signals from the measurement points, thereby obtaining the skin impedance;
   a microcontroller processor; and
   a computing memory, which stores instructions executed by the microcontroller processor;
   when the instruction is executed by the microcontroller processor, the following steps are executed:
   calculating the difference between a forward skin impedance measured using a forward DC voltage and a reverse skin impedance measured using a reverse DC voltage;
   determining whether measurement results are abnormal by continuously measuring the forward skin impedances, the reverse skin impedances, and their differences;
   correcting abnormal results by adjusting the magnitudes and time durations of the DC voltages, and/or applying additional AC voltages of adjustable frequencies and magnitudes of AC voltages;
   remeasuring the skin impedances to check if the differences between the forward skin impedance and the reverse skin impedance are reduced to a preset threshold to ensure an accuracy of the measurement data; and
   a display unit for displaying measurement results.

2. The system of claim 1, wherein when the measurement result is abnormal and the abnormal results cannot be corrected through applying forward or reverse DC or AC voltages, the following instruction is further executed by the microcontroller processor:
   store the forward skin impedance and reverse skin impedance, calculate weighted arithmetic and geometric averages of these two impedances and estimate skin impedance as the medical evidence for following diagnosis and treatment.

3. The system of claim 1, wherein the electrodes are silver/silver chloride (Ag/AgCl) electrodes.

4. The system of claim 1, wherein the electrodes are a polarized electrode.

5. The system of claim 1, wherein the electrodes are metal electrodes.

6. The system of claim 1, wherein the electrode measurement is implemented through a double-electrode impedance measurement method.

7. The system of claim 1, wherein the electrode measurement is implemented through a multi-electrode impedance measurement method.

8. The system of claim 1, wherein the electrode group comprises a stimulating electrode and a reference electrode, wherein the adjustable voltage output unit generates step-function DC voltages, applying on the stimulating electrode, forming forward or reverse voltages between the stimulating electrode and the reference electrode.

9. The system of claim 1, wherein the skin impedance measurement unit, is configured to include an amplification and filter circuit and an A/D converter when measuring one channel of skin impedance;
   is configured to include voltage multiplexers, one or more A/D converters when measuring multiple channels of skin impedances, in addition to amplification and filter circuit.

10. The system of claim 1, wherein the variables to control the adjustable voltage output unit include:
    the time duration of the forward and reverse voltages applied between the electrodes.

11. The system of claim 1, wherein the variables to control the adjustable voltage output unit include:
    the magnitude of the forward and reverse voltages applied between the electrodes.

12. The system of claim 10, wherein changing the time duration of the forward voltage and the reverse voltage applied between the electrodes includes one or more of the following measures:
    increase the time duration of the applied forward voltage;
    decrease the time duration of the applied forward voltage;
    increase the time duration of the applied reverse voltage;
    decrease the time duration of the applied reverse voltage.

13. The system of claim 11, wherein changing the magnitude of the forward voltage and the reverse voltage applied between the electrodes includes one or more of the following measures:
    increase the magnitude of the applied forward voltage;
    decrease the magnitude of the applied forward voltage;
    increase the magnitude of the applied reverse voltage;
    decrease the magnitude of the applied reverse voltage.

14. The system of claim 1, wherein the controlling signal to control the adjustable voltage output unit comprises:
    forward and/or reverse DC voltages with different magnitude and time duration, to reduce the polarization phenomenon during the impedance measurement through electrodes; or
    AC voltages with different magnitude, frequency and duration to reduce the polarization phenomenon of the system before or after forward and/or reverse DC voltages.

15. The system of claim 1, wherein the AC voltage is a square wave, a triangular wave, a sine wave, or other waveforms whose frequency and magnitude is adjustable.

16. The system of claim 1, when the measurement result is abnormal, further comprising a signal generating system to control the adjustable voltage output unit to output AC voltages with adjustable frequencies, magnitudes, and duration; the AC voltages are then applied to the skin through the electrodes to minimize the abnormal measurement results; if the measured difference between forward and reverse skin impedance values cannot be reduced to a preset threshold, the system will record both values for later analysis to assist future diagnosis and treatment; electrical stimulations of different waveforms further treat the patient with pathological changes.

17. A method for measuring skin impedance, comprising:
applying step-function DC voltages of various magnitudes to the stimulating electrode, to form forward and reverse DC voltages between stimulating and reference electrodes and conducting the voltage to the skin through electrodes;
measuring the forward skin impedance and reverse skin impedance with forward and reverse DC voltages;
determining whether the measured results are abnormal based on the differences between the forward and reverse skin impedances;
correcting abnormal results by adjusting the magnitudes and time duration of the step-function DC voltages, and/or generating additional AC voltages of adjustable magnitude and frequency based on the difference of the forward and reverse skin impedances, applying these voltages to the skin through electrodes;
remeasuring the skin impedance to check if the forward and reverse skin impedance difference is reduced to a preset small range;
if the difference between the forward and reverse skin impedance cannot be reduced below a threshold, recording the forward and reverse skin impedances, calculating arithmetic and geometric averages to estimate the true skin impedance and provide as clinical evidence for future diagnosis and therapy.

* * * * *